United States Patent [19]
McCabe, Jr. et al.

[11] 4,078,433
[45] Mar. 14, 1978

[54] LIQUID SAMPLING DEVICE

[75] Inventors: Joseph H. McCabe, Jr., Short Hills, N.J.; Joseph Martella; Arthur Handt, both of Brooklyn, N.Y.

[73] Assignee: E. W. Saybolt & Co., Inc., Kenilworth, N.J.

[21] Appl. No.: 763,755

[22] Filed: Jan. 28, 1977

[51] Int. Cl.² .............................................. G01N 1/12
[52] U.S. Cl. .............................................. 73/425.4 R
[58] Field of Search .................................. 73/425.4 R

[56] References Cited

U.S. PATENT DOCUMENTS

| 1,610,459 | 12/1926 | McBride | 73/425.4 R |
| 1,759,444 | 5/1930 | Dunn et al. | 73/425.4 R |
| 2,388,548 | 11/1945 | Jors | 73/425.4 R |

*Primary Examiner*—S. Clement Swisher

*Attorney, Agent, or Firm*—C. Bruce Hamburg

[57] ABSTRACT

A liquid sampling device comprises a length of pipe having a cap screwed onto each end thereof. The device is provided with means for suspending it with the axis of the pipe oriented vertically. The upper cap has an aperture for admitting the liquid to be sampled. The lower cap has an aperture and a stopcock which may be opened to permit the sampled liquid to flow out of the device for inspecting and testing. The flow resistance of the aperture, generally determined by the diameter thereof, and the volumetric capacity of the device relative to the viscosity of the liquid and the depth of a body thereof to be sampled will be selected so that when the device is lowered to the bottom of the body of liquid and then lifted out therefrom, the device will not fill to capacity, whereby a representative sampling is assured throughout the depth of the body of liquid.

1 Claim, 3 Drawing Figures

LIQUID SAMPLING DEVICE

BACKGROUND OF THE INVENTION

This invention relates to a liquid sampling device. More particularly, this invention relates to a device for sampling a static body of liquid.

There is a frequent need to sample a static body of liquid, such as a liquid contained in a storage tank, to assure that it meets specification. It is desired that the sample of liquid drawn from the static body of liquid for this purpose be constituted of liquid from all depths in the body.

Numerous liquid sampling devices are disclosed in the prior art. Representative of these are the following U.S. Pat. Nos. 832,164; 1,416,354; 1,511,591; 1,539,790; 1,585,072; 1,606,104; 1,769,533; 2,198,116; 2,223,598; 2,388,548.

While some of these devices do not sample liquid from all depths of the body, others indeed to. However, the devices tend to be complicated and, consequently, relatively expensive and subject to possible malfunction and in many instances also tend to be quite bulky or lengthy, which is an additional disadvantage.

It is an object of the present invention to provide a device for sampling a static body of liquid which will take up liquid from all depths of the body to thereby obtain a representative sample and be simple in construction, relatively inexpensive, compact and trouble-free.

Other objects and advantages of the present invention will be apparent from the following description.

SUMMARY OF THE INVENTION

According to the invention, there is provided a device for sampling a static body of liquid comprising an imperforate length of pipe having threads at each end and respective threaded closures screwed onto the ends of the pipe with the threads of the closures engaging the threads of the ends of the pipe. The device also includes means for suspending the device with the axis of the pipe oriented vertically. Respective apertures are formed in the two closures. The lower closure is associated with valve means communicating with the aperture in the lower closure for alternatively preventing and permitting flow through the aperture of any liquid contained in the device. The device is imperforate apart from the respective apertures in the two closures. The diameter and axial length, in other words, the flow resistance, of the aperture in the upper closure and the volumetric capacity of the device are so selected relative to the average viscosity of the liquid to be sampled and the depth of the body thereof that when the valve means is closed and the device is suspended from pliable elongated means, such as a rope, cable or chain, connected to the suspending means, dropped into the body of liquid, permitted to sink to the bottom thereof and then manually pulled through and out of the body of liquid, the liquid will enter the device through the aperture in the upper closure continuously throughout its passage through the body of liquid, but the total volume of the liquid entering the device will be less than the volumetric capacity of the device.

The valve means may particularly conveniently be a stopcock. A particularly convenient, inexpensive, easy to assemble and disassemble construction is attained when the threads at both ends of the pipe are external and the threads of both closures are internal, each of the closures is in the form of a cap having an annular side wall integral with an end wall, the threads of the closure being formed on the internal surface of the annular side wall, the respective aperature of each of the closures passes through the end wall thereof, and the suspending means is connected to the upper closure.

BRIEF DESCRIPTION OF THE DRAWINGS

The invention will now be further described by reference to a specific embodiment as illustrated in the drawings, in which.

DESCRIPTION OF THE PREFERRED EMBODIMENT

Figure 1:
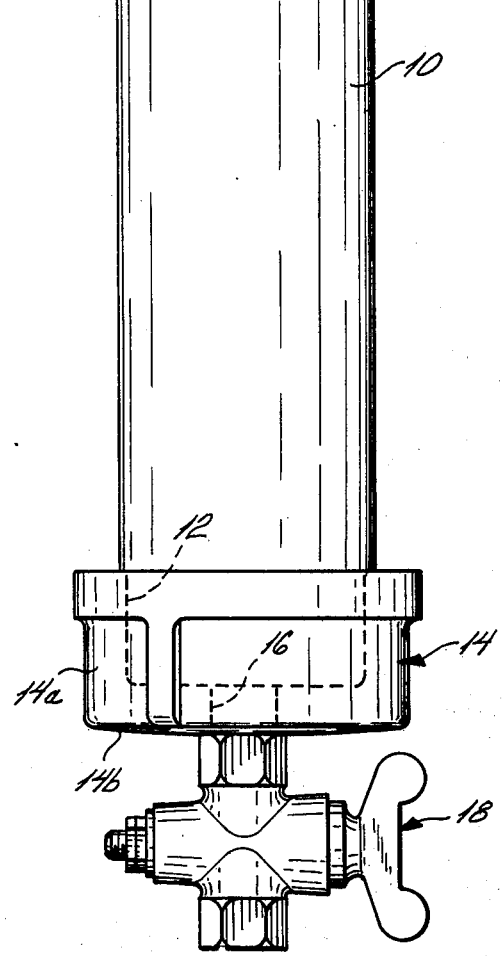
FIG. 1 is an elevation of a liquid sampling device according to the invention.
Figure 2:
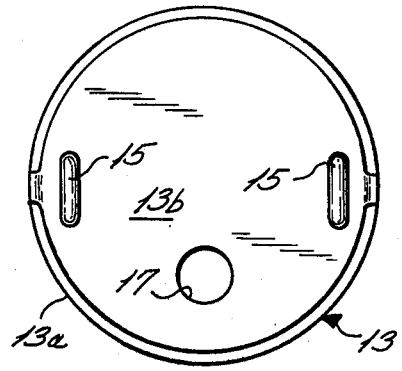
FIG. 2 is a top plan view of the device of FIG. 1.
Figure 3:
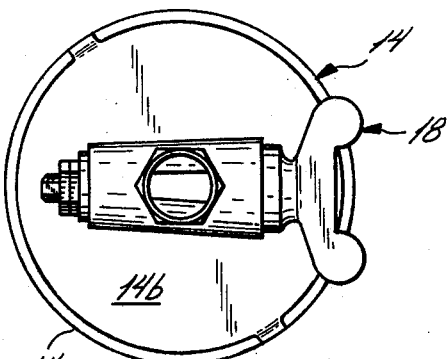
FIG. 3 is bottom plan view of the device of FIG. 1.

The main body of the device is constituted of a length of pipe 10 having externally threaded ends 11 and 12 (FIG. 1). When the device is used to sample a liquid, it will be oriented vertically with the upper end being end 11 and lower end being end 12; therefore, for convenience, these ends will be referred to as "upper" and "lower", respectively. Screwed onto the upper threaded end 11 is a closure 13, and screwed onto the lower threaded end 12 is a closure 14. Closures 13 and 14 are each in the form of a cap having a respective annular side wall 13a or 14a integral with the respective end wall 13b or 14b (FIGS. 1 to 3). Each of the caps 13 and 14 is internally threaded, the threads of the caps being formed on the internal surface of the annular side wall thereof, the threads of each of the caps engaging the threads on the respective ends of the pipe 10.

The suspending means is in the form of a pair of closed rigid wire hooks 15 connected to the cap 13 and a rigid wire hanger member 16 having looped ends 16a and 16b engaging the closed hooks 15 in the manner of chain links. The hanger member 16 is also formed into a loop 16c by means of which a rope, cable, chain or other pliable elongated member may readily be fastened to the hanger member 16 in order to suspend the liquid sampling device of the invention therefrom.

The upper cap 13 has an aperture 17 therethrough. The lower cap 14 has an aperture 16 therethrough which communicates with a stopcock 18.

When a sample is to be taken, the liquid sampling device is quickly lowered to the bottom of the body of liquid to be sampled, such as a tank, and thereafter quickly raised and lifted out of the liquid. The device is designed according to the viscosity of the liquid to be sampled and the depth of the body thereof so that it does not fill to capacity during the lowering and opening. The design parameters are the diameter of the aperture 17 and the volumetric capacity of the device. The volumetric capacity can readily be changed by substituting a different length of pipe 10. A third parameter is optionally available. Specifically, the aperture 17 may be internally threaded and there may be provided a set of externally threaded nipples of varying length, say, for example, $\frac{1}{2}$ inch, one inch, 1 $\frac{1}{2}$ inches and so forth. Addition of these nipples will, in effect, convert 17 from a simple aperture to a conduit the flow resistance of which is significantly affected by the length thereof. Merely by way of example, the dimensions are given of a liquid sampling device of the invention particularly suitable for sampling a 20 foot deep body of No. 6 oil: diameter of the aperture 17, $\frac{1}{2}$ inch; internal depth of the device, including the caps about 7 inches; internal diameter of the device, about 2 inches. If the device would fill to capacity, one could not assume that the liquid contained in the device was a representative sample since the device may have filled, and probably did fill, before it completed its passage through the depth of the body of liquid.

Operation of the device is, of course, exceedingly simple. The stopcock is closed. The device is quickly lowered to the bottom of the body of liquid and lifted therefrom. The sampling device containing the liquid is then brought to wherever inspection and testing is to take place. The stopcock is opened to empty the liquid into a suitable vessel in which it may be inspected and/or tested.

While the invention has been described with reference to a specific embodiment, it is understood that this embodiment is intended to illustrate rather than the limit the invention and that the invention is defined by the hereto appended claims.

What we claim is:

1. A device for sampling a static body of liquid constituted in its entirety of an imperforate length of pipe having external threads at each end, a first cap having an end wall and integral therewith an internally threaded annular side wall, said first cap being screwed onto one end of the pipe with the threads of said first cap engaging the threads of said one end of the pipe, a second cap having an end wall and integral therewith an internally threaded annular side wall, said second cap being screwed onto the other end of the pipe with the threads of said second cap engaging the threads of said other end of the pipe, means for suspending the device with the axis of the pipe oriented vertically and the second cap at the lower end of the pipe, said suspending means comprising a pair of closed rigid wire hooks connected to the first cap at diametrically opposed locations on the end wall of the first cap and a rigid wire hanger member having looped ends engaging the closed hooks and a loop formed at the middle, said middle loop being adapted to be engaged by a pliable elongated member for suspending the sampling device, an aperture formed through the end wall of the second cap, a stopcock communicating with the aperture for alternatively preventing and permitting flow through the aperture of any liquid contained in the device, and an aperture formed through the end wall of the first cap, the device being imperforate apart from the respective apertures in the first and second caps, the diameter and axial length of the aperture in the first cap and the volumetric capacity of the device being so selected relative to the average viscosity of the liquid to be sampled and the depth of the body thereof that when the stopcock is closed and the device is suspended from pliable elongated means connected to said middle loop of said wire hanger member, dropped into the body of liquid, permitted to sink to the bottom thereof and then manually pulled up through and out of the body of liquid, the liquid will enter the device through the aperture in the first cap continuously throughout its passage through the body of liquid but the total volume of liquid entering the device will be less than the volumetric capacity of the device.

* * * * *